United States Patent [19]
Heckele et al.

[11] Patent Number: 5,582,575
[45] Date of Patent: Dec. 10, 1996

[54] INSTRUMENT FOR ENDOSCOPIC THERAPY

[75] Inventors: Helmut Heckele; Uwe Schaumann, both of Knittlingen; Benno Kunert, Mühlacker; Martin Seebach, Obererdingen, all of Germany

[73] Assignee: Richard Wolf GmbH, Knittlingen, Germany

[21] Appl. No.: 393,070

[22] Filed: Feb. 23, 1995

[30] Foreign Application Priority Data

Feb. 23, 1994 [DE] Germany ................... 44 05 720.2

[51] Int. Cl.⁶ ........................................... A61B 1/00
[52] U.S. Cl. ..................... 600/104; 600/105; 600/137; 600/175
[58] Field of Search .................... 600/104, 105, 600/113, 127, 129, 135, 136, 137, 138, 175; 606/27, 28, 29, 39, 46, 170; 604/158

[56] References Cited

U.S. PATENT DOCUMENTS 3,368,552  2/1968  Böttcher .
4,974,580  12/1990  Anapliotis .

*Primary Examiner*—Linda C. Dvorak
*Assistant Examiner*—Beverly M. Flanagan
*Attorney, Agent, or Firm*—Cohen, Pontani, Lieberman, Pavane

[57] ABSTRACT

An endoscope having a longitudinally-slotted probe that is connected to a guidance part for an optical system which extends in an axially movable fashion through the guidance part into the probe and the view of which is directed toward the longitudinal slot of the probe. The axial adjustment of an associated optical system is operated by a drive, which is connected to the guidance part and can be operated by hand. The instrument can be held by an operator using one hand and, as this is done, the optical system can be securely brought into position. The optical system can be adjusted using this same hand, thus permitting the operator to use the other hand to guide a surgical instrument.

13 Claims, 2 Drawing Sheets

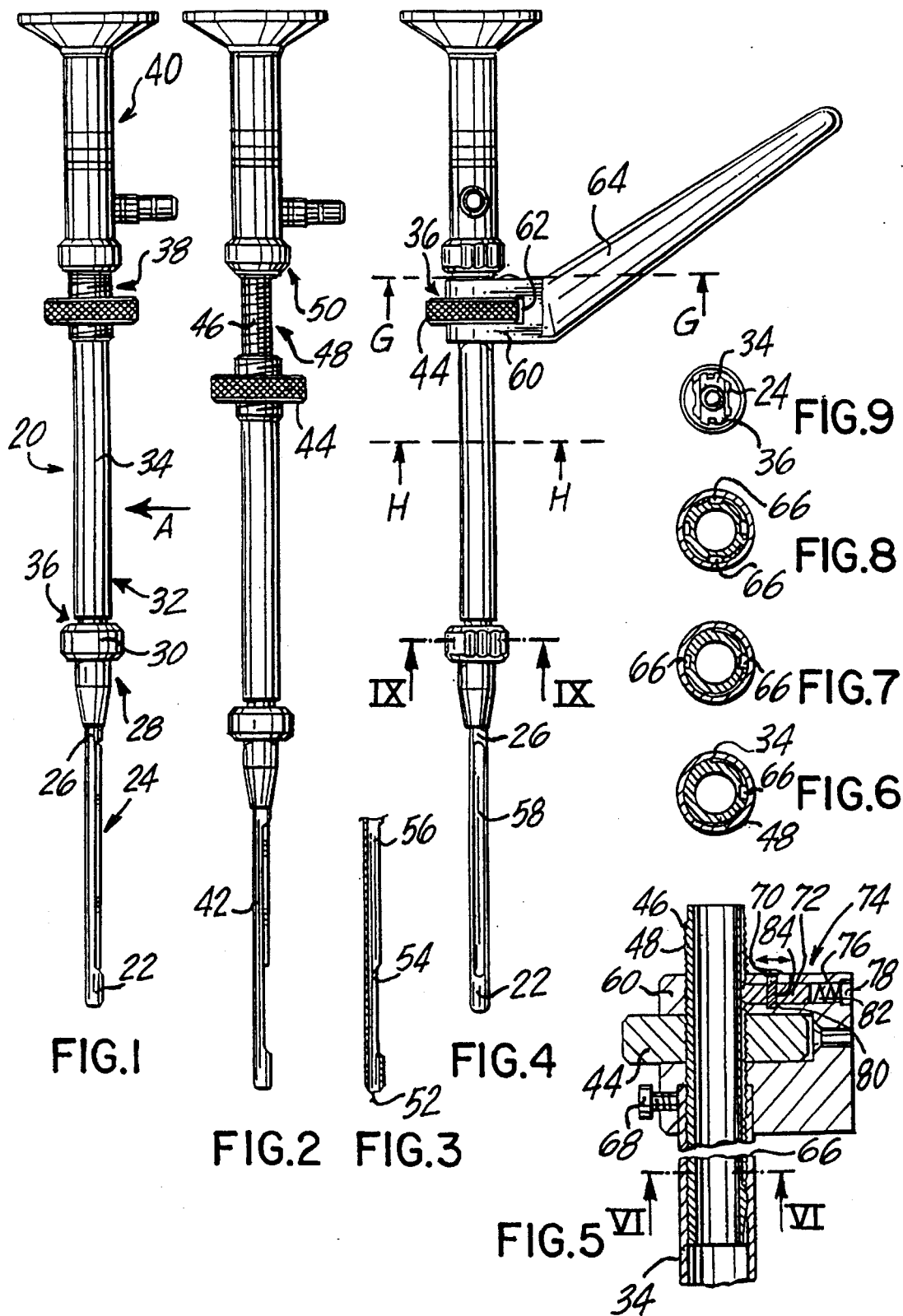

INSTRUMENT FOR ENDOSCOPIC THERAPY

BACKGROUND OF THE INVENTION

1. Field of the Invention

The present invention relates to an endoscope, and more particularly, an instrument for endoscopic therapy having a longitudinally-slotted probe connected to a guidance part to accommodate for example, an optical system, which is interposed within the guidance part in an axially movable fashion and which extends into the probe to permit viewing through the optical system to be directed toward the longitudinal slot of the probe.

2. Description of the Prior Art

Surgical or diagnostic procedures of the invasive types are usually, and justifiably, a choice of last resort for both the patient and his or her physician. One reason is that such procedures are traumatic to the patients and thus necessitate the administration of expensive anesthetics—local or, even, general. Another reason is that complications such as infections may ensue, thereby making post-operative care critically important.

Having mentioned some of the drawbacks of invasive procedures, one appreciates the value of surgical techniques known as minimally invasive procedures. These procedures recognize the fact that at times invasive surgical or diagnostic procedures are inevitable. However, the trauma or associated complications can be dramatically reduced if the number of incisions in the epidermis are kept to a minimum such, for example, as in a single-portal procedure which requires only a single incision, as opposed to a two-portal procedure, which requires an entry incision and an exit incision. Additionally, in this age of ever-increasing medical expenses, a procedure which is cost-efficient as a result of permitting surgery by a single physician as opposed to two or more physicians is highly desirable. To that end, an instrument which enables a single physician to perform a single-portal procedure is highly desirable.

WO 93/10 704 discloses an endoscopic instrument which is utilized in a two-portal procedure for the treatment of carpal tunnel syndrome, a peripheral neuropathy which is characterized by sensory loss, muscle weakness and atrophy, among other symptoms, in the hand and wrist area. The endoscopic instrument has a probe with a longitudinal slot which is introduced during the procedure into the entrance portal and brought out of the exit portal. To facilitate observation of the surgical area, a video arthroscope can be inserted into the distal end of the probe, which extends out of the entrance portal. The operative procedures are performed by introduction of suitable scalpel-type instruments from the proximal side of the probe. As a general rule, the surgical procedure utilizing this instrument requires that one operator performs the operation while a second operator is responsible for guiding the video arthroscope.

European Patent Application EP-A-0 552 980 discloses an instrument for use in the so-called single-portal procedure for treating carpal tunnel syndrome. This instrument is comprised of a hollow probe closed at the distal end and having a longitudinal recess therein which permits the introduction of a suitable surgical instrument, such as a scalpel. The proximal end of the probe allows the introduction of an optical system for observing the operation. The disadvantage of this device is that optimum work is possible only when two operators work together.

Reference to anatomical factors and requirements in the treatment of carpal tunnel syndrome is also made in U.S. Pat. No. 5,029,573, which describes another instrument for the two-portal procedure, as well as in U.S. Pat. No. 4,962,770 and U.S. Patent No. 4,963,147, both of which disclose instruments for the single-portal procedure. The operative method of surgery utilizing endoscopic devices is known to those skilled in the art and is described in European Patent Application EP-A-552 980 and thus need not be discussed here.

The instruments according to this prior art, are generally disadvantageous in that two operators are always needed to perform an operation. Furthermore, in the two-portal procedure, the need to make two incisions, thus placing additional traumatic stress on the patient, must be seen as disadvantageous. Similar problems result when instruments of this type are used, for example, in treating paralysis of the radial nerve and other neuropathological conditions.

Therefore, it is an object of the present invention to provide an endoscopic instrument for diagnosis and treatment that requires only one incision and can be operated simply and by a single operator. Furthermore, the instrument is to be equally operable by left-handed and right-handed persons. Another object of the invention is to provide an endoscopic instrument which is comparatively stable and can be easily disassembled to allow for optimum cleanliness and disinfection.

SUMMARY OF THE INVENTION

The present invention provides an endoscopic instrument having a probe to accommodate an optical system which is axially adjustable by means of a drive, which is associated with a guidance part and can be operated by hand. The guidance part may be comprised of a tubular shaft and can include a guidance sleeve, which is axially movable within the tubular shaft and through which the optical system runs. In the completely assembled embodiment, there are generally two coupling mechanisms, one coupling mechanism which connects the optical system to the guidance sleeve, and a second coupling mechanism which connects the shaft to the probe. Furthermore, the tubular shaft is detachably connected to the probe and the guidance sleeve is detachably connected to the optical system. Easy adjustability of the optical system, which is generally an especially delicate device, is attained when the guidance sleeve is provided on its outer circumference with a screw thread and a drive means having a nut, preferably a knurled nut, which engages into this screw thread.

An instrument constructed in this manner can be securely held by an operator in one hand, while the operator uses, for example, the thumb and forefinger of this same hand to axially adjust the optical system by rotation of the nut of the drive means. The operator can thus use the optical system, for example, to follow the incision of the scalpel, the free end of the optical system which is conducted in the slot of the probe, while simultaneously operating the scalpel with his other hand. The instrument of the present invention can be used in this manner by left-handed and right-handed persons alike, because the nut is conducted in a housing connected to the shaft and projects beyond the housing with its periphery on multiple sides.

The construction of the instrument from parts connected to one another in a detachable fashion permits its simple disassembly into individual parts, which can then be easily cleaned and sterilized.

DETAILED DESCRIPTION OF THE DRAWINGS

An understanding of the present invention will be facilitated by the detailed description of the presently preferred embodiment set forth herein taken together with the annexed drawings in which:

FIG. 1 is a side elevational view of the complete instrument with the optical system in the extreme distal position;

FIG. 2 is a view of the instrument as in FIG. 1 with optical system only partially extended toward the proximal direction;

FIG. 3 is a fragmentary view of the probe of the instrument as in FIG. 2 in partial longitudinal section;

FIG. 4 is an elevational view of the instrument as in FIG. 1, looking in the direction of the arrow A in FIG. 1;

FIG. 5 is an longitudinal sectional of a part of G—G and H—H on FIG. 4. in the area of the drive means, shown in enlarged scale;

FIG. 6 is a cross-sectional view through the shaft of the instrument along Line VI—VI as shown in FIG. 5;

FIG. 7 is a cross-sectional view through the instrument according to FIG. 6, modified for left-handed and right-handed operation by the inclusion in the guidance sleeve of two longitudinal slots;

FIG. 8 is a sectional view of the configuration of FIG. 6, showing the guidance sleeve with four longitudinal slots;

FIG. 9 is a cross-sectional view through the coupling mechanism along Line IX—IX as shown in FIG. 1;

Figure 10:
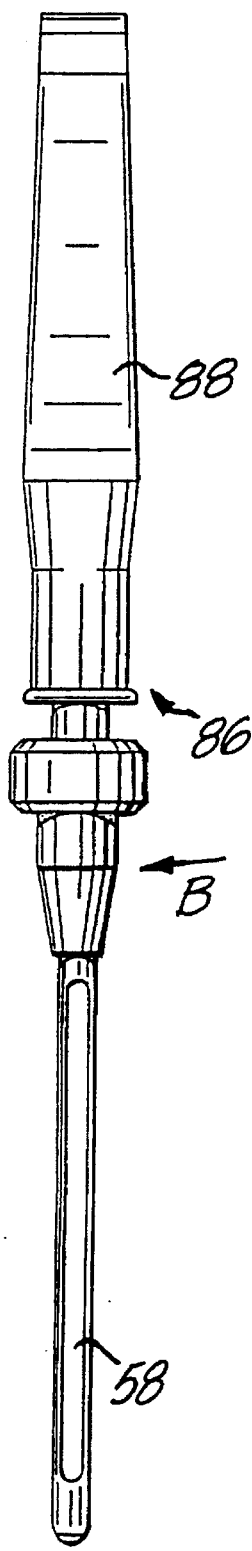
FIG. 10 is a view of the probe detached from the instrument as in FIG. 1, with an obturator connected to it.

It is to be understood that the drawings are designed solely for the purposes of illustration and not as a definition of the limits of the invention, for which reference should be made to the appended claims.

DETAILED DESCRIPTION OF THE PRESENTLY PREFERRED EMBODIMENT

Referring now to the drawings in detail, there is shown the endoscopic instrument according to the invention 20. The instrument, as seen in its presently preferred embodiment shown in FIGS. 1, 2 and 4, is comprised of a probe 24, a guidance part 32 with a drive means 38, and a handle 64 (shown in FIG. 4), as well as an optical system 40 (shown in FIG. 1) and a guidance sleeve 48 (shown in FIG. 2) connected to the optical system.

The probe 24 is comprised of an insertion sleeve 42 with a longitudinal slot 58, a distal end 22 of probe 24 is configured in a rounded fashion which has an opening 52 therein. The longitudinal slot 58 is in communication with the axial opening 52 and thus terminates at the distal end 22.

Probe 24 also has a proximal end 26 where is located a first coupling mechanism 28 with a locking ring 30 for detachably connecting the probe 24 to the distal end of the guidance part 32 as by any suitable connection such as, for example, a threaded connection, a bayonet connection, a press fit connection, or any other form of connection. This embodiment of the connecting element preferably ensures that the probe 24 and the guidance part 32 can be connected to one another in a pre-determined radial relationship and in a rotation-proof manner, such as by the use of a key and slot in the connection.

The guidance part 32 has a tubular shaft 34, the proximal end area of which has a housing 60, which serves first as the mounting base for the handle 64 and second to accommodate the drive means 38 (FIG. 4). The drive means 38 is formed by a spindle drive from a nut 44, disposed in a recess 62 of the housing 60 which runs transverse to the tubular shaft 34. The axis of the nut 44 and the tubular shaft 34 are aligned with another. Nut 44 has a central aperture extending. perpendicularly through its centerpoint (not shown).

Running longitudinally in the interior of the guidance part 32 is a guidance sleeve 48 shown in FIGS. 5 and 6, which has a screw thread on its outer circumference (not shown). The interior circumference of the aperture of the nut 44 is provided with a thread that is complementary to screw thread 46 on the guidance sleeve 48 and is threadedly engaged therewith. The guidance sleeve 48 also has a longitudinal slot 66, and preferably a second longitudinal slot 67 as shown in FIG 7. The two longitudinal slots run from at or near the proximal end of the guidance sleeve 48 to at or near its distal end. The longitudinal slots 66 and 67 subdivide the screw thread 46 thereby interrupting the thread turn which engages the nut 44.

A locking mechanism 74 is arranged in the housing 60 for releasably engaging one or the other of the longitudinal slots 66 and 67 in the guidance sleeve 48 to thereby prevent unwanted rotation of the sleeve. This locking mechanism is designated by the reference numeral 74 and is shown best in FIG. 5 to include a detent or locking pin 72 slidably disposed in a bore or aperture 82. The pin 72 is spring pressed by a compression spring 76 also located in the bore 82 and held at the outer end thereof by a stop 78. To retract the detent or pin 72 in order to permit rotation of guidance sleeve 48, an operating element 70 in the form of a screw or the like is provided. This operating element extends through an elongated slot in the top of the housing 60 and through a complementary hole or bore 84 in the detent or pin 72 and then into a blind hole 80 in housing 60 that aligns with the aperture 82 and pin 72 when the pin is in its fully extended position inside of one of the longitudinal slots 66 in the guidance sleeve 48. To retract the detent or pin 72 from one of the slots 66 and 67 to free sleeve 48 for rotation, the operating element 70 must be raised to withdraw the distal end thereof from the blind hole 80 and the pin 72 is then pushed or pulled to the right as viewed in FIG. 5 whereby to push it against the compression spring 76 to remove it from the slot 66. Thereafter, after rotation of 180° has been accomplished, the pin will be returned to the slot 66 by the urging of the spring 76.

In alternative embodiments of the present invention the guidance sleeve may have a more than two, e g "n" longitudinal slots thereon, into which the locking pin 72 can fit. The longitudinal slots are preferably spaced from one another in angular increments of 360/n degrees around the circumference of the guidance sleeve (see FIG. 8 which shows four slots).

At its proximal end, the guidance sleeve 48 has a second coupling mechanism 50 (FIG. 2), which is structurally similar to the first coupling mechanism 28 at the proximal end 26 of the probe 24 (FIG. 1). This second coupling mechanism 50 constitutes a detachable connection between guidance sleeve 48 and the optical system 40.

In the completely assembled instrument, the optical system 40 has a shaft 56, disposed within the guidance sleeve 48 and extends through the tubular shaft 34 into the probe 24. The shaft of the optical system 56 is disposed within the insertion sleeve 42 of the probe 24 for guidance thereby. On the distal end of the optical shaft 56 there exists a lens window 54 to permit viewing of the surgical procedure through the optical system 40. (FIG. 3).

Figure 11:
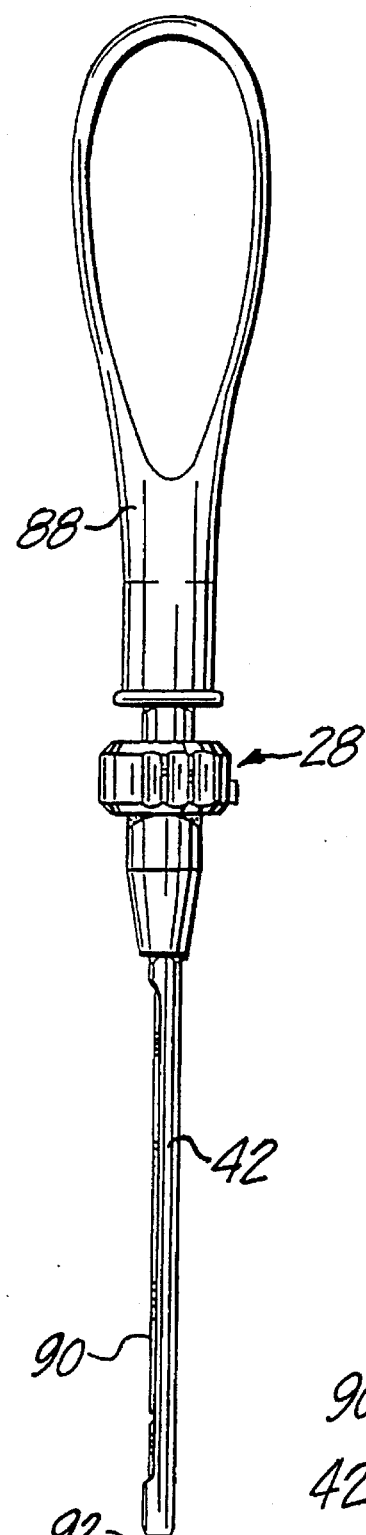
FIG. 11 is a view of the probe as in FIG. 10, looking in the direction of the arrow B in FIG. 10.
Figure 12:
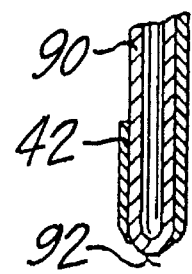
FIG. 12 is an enlarged longitudinal sectional fragmentary view, through the distal end area of the instrument as in FIG. 11.

In preparation for surgical intervention, the probe 24 is first connected by means of the coupling mechanism 28 to an obturator 86 (FIGS. 10 and 11), to permit atraumatic insertion of the probe through an operatively-created incision. The obturator 86 is comprised of a handle 88 with a shaft 90 which is rounded on its distal end 92 and, which can be slid into the insertion sleeve 42 of the probe 24. The structural lengths of the obturator shaft 90 and the probe 24 are related to one another in such a way that the distal end 92 of the obturator emerges from the axial opening 52 of the insertion sleeve 42 just as the final or fully inserted position is reached. After insertion of the probe 24 into an incision made in the patient undergoing the surgical procedure, the obturator 86 is extracted from the probe 24 and can be replaced by an optical system 40, which views straight through the axial opening 52 and laterally through the longitudinal slot 58 of the probe (FIGS. 1–3). For this purpose, the guidance part 32, pre-assembled with the shaft 34, the drive means 38, the guidance sleeve 48 and the optical system 40, is preferably connected by means of the first coupling mechanism 28 to the probe 24.

To change the viewing field of the optical system, the optical system 40 is movable in a longitudinal direction by turning the nut 44 of the drive means 38 (FIG. 4). The proximal final position is pre-established by the fact that the pin 72 of the locking mechanism 74 strikes against the distal end of the longitudinal slot 66 or 67 (FIG. 5). This interference with the distal end of the longitudinal slot 66 by the pin 72 also prevents the guidance sleeve 48 and the shaft 34 from separating.

The desired position of the lens window 54 relative to the longitudinal slot 58 of the probe 24 is achieved by a 180° turn of the guidance sleeve 48 and the probe 24. A locking ring 30, which is part of the coupling mechanism 28, can be tightened and loosened to adjust and maintain the desired position of the probe 24.

The presently preferred embodiment of the invention permits adjustment of the optical system 40 with one hand by the operator, to partially withdraw the shaft 56 in the proximal direction so that the other hand remains free in order, for example, in treating carpal tunnel system, to introduce a surgical cutting instrument into the longitudinal slot 58 of the probe 24 after the shaft 56 has been withdrawn a sufficient distance to allow insertion of the surgical instrument. The surgical procedure can then be observed by tracking with the optical system 40 using the drive means 38. During the surgical procedure, the surgical instrument is conducted in the longitudinal slot 58 and is prohibited from slipping sideways by the walls of the longitudinal slot.

The instrument of the present invention is easily disassembled for purposes of cleaning and sterilization. By detaching the coupling mechanisms 28 and 50, the probe 24, the guidance part 32 and the optical system 40 are easily detached from each other.

Furthermore, the guidance part 32, the guidance sleeve 48 and the drive means 38 can also be separated from one another. The drive means 38 is located within the housing 60 located just distally of the coupling mechanism 50. Within the housing 60 is a pin 72 which is part of the aforementioned locking mechanism 74, which as previously discussed, is used in conjunction with the operating element 70, for adjusting the rotation of the optical system. By manipulating the operating element 70, the pin 72 can be caused to retract in the locking mechanism 74. This eliminates the limit to the slide path set by the end of the longitudinal slot 66 of the guidance sleeve 48 and permits the guidance sleeve 48 to be removed from the guidance part 32 and the drive means 38 by turning the nut 44 in a loosening direction.

The instrument of the present invention permits easy operation instrument by left-handed and right-handed persons alike. To facilitate this ambidextrous use, the nut 44, which is located in a recess of the housing 62, is designed so that its periphery projects beyond the recess 62 of the housing 60 on multiple sides. This arrangement permits easy rotation of the nut 44 by the operator's thumb finger. The embodiment shown in FIG. 4 depicts the instrument in an assembly suitable for a right-handed person. For operation by a left-handed person, the instrument must be turned by 180° relative to FIG. 4 so that the handle 64 would be on the left thus allowing the operator's left hand thumb to rotate the nut 44.

In FIG. 1 and the cross-section of the coupling mechanism 28 shown in FIG. 9, it can be seen that the proximal end of the probe 26 is axially aligned with the tubular shaft 34 and thus engages in a positive-locking manner with the tubular shaft 34 at its distal end 36. Connection in this manner permits 180° revolution of the probe 24, since the probe 24 and the guidance part 32, within which the tubular shaft 34 coexists, are connected to one another in a pre-established relationship in a rotation-proof fashion.

In accordance with the presently preferred embodiment of the invention, the guidance sleeve 48 has two longitudinal slots 66 which extend along the axial length of the guidance sleeve 48 and which are staggered by 180° (FIG. 7). After the pin 72 of the locking mechanism 74 located in the housing 60 is retracted from its engagement within one of the longitudinal slots 66 (FIG. 5), the optical system 40 can be turned by 180°. It is also conceivable for the coupling mechanism 50 to allow turning between the optical system 40 and the guidance sleeve 48.

In FIG. 8 there is shown a further modification of the instrument, which permits the optical system 40, to be turned in 90° increments, since four longitudinal slots 66 are provided for selective engagement by the pin 72.

Additionally, the radial direction of the instrument can be altered without changes in the positions of the coupling mechanisms. To permit this, the shaft 34 is rotatably established within the housing 60. This arrangement is made possible by a deactivatable rotation-lock using a clamping screw 68, with which the shaft 34 can be fixed in place in the housing 60 (FIG. 5). To ensure that the guidance part 32 and the guidance sleeve 48 are turned in the same direction, the aforementioned pin 72 of the tubular shaft 34 engages one of the longitudinal slots 66 which extend along the length of the guidance sleeve 48. By loosening the clamping screw 68 which is embedded in the upper area of the tubular shaft 34 located just distal to the nut 44, the probe 24 can be turned simultaneously with the optical system via the guidance part 32 and the guidance sleeve 48.

In operation, because of the rotatability of the probe 24 and the optical system 40, the instrument permits increased flexibility in positioning the guidance sleeve 48 and also allows an attached light source connection to be positioned so that the operator is not disturbed by lighting cable. As a result, the instrument of the present invention can be used not only for treating carpal tunnel syndrome but also for further indications, for example, in treating paralysis of the radial nerve.

Thus, while there have been shown and described and pointed out fundamental novel features of the invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

It is to be understood that the drawings are not necessarily drawn to scale, but that they are merely conceptual in nature.

What is claimed is:

1. An endoscope comprising:
 a longitudinally extending probe having a proximal end, a distal end, and a longitudinal slot extending partially therethrough along one side, and wherein said proximal end is configured for supporting an optical system thereon;
 a cylindrical guidance part having a proximal end and a distal end, said guidance part including a tubular shaft having a proximal end and a distal end with a bore extending therethrough, wherein the distal end of said tubular shaft is detachably connected to the proximal end of said longitudinally extending probe, and a guidance sleeve disposed within said tubular shaft capable of axial movement for receiving an optical system;
 a housing, connected to the proximal end of said tubular shaft, having a recess therein, a drive means for said tubular shaft rotatably mounted in said recess, said drive means being rotatably disposed about said guidance part, and means for connecting said drive to said guidance sleeve for imparting rotation to said guidance sleeve in response to rotation of said drive means.

2. The endoscope as recited in claim 1, wherein said guidance sleeve is detachably connectable to an optical system, and wherein said optical system may be manipulated by rotating said guidance sleeve via said drive means.

3. The endoscope as recited in claim 1, wherein said drive means comprises a nut disposed in said recess of said housing, said nut having an aperture extending axially therethrough, the internal wall of said aperture of said nut being threaded, the guidance sleeve having a threaded external surface complementary to and interfitting with said thread on the aperture wall of said nut.

4. The endoscope as recited in claim 3, wherein the outer periphery of said nut is knurled and has a radius greater than said recess of said housing.

5. The endoscope as recited in claim 1, further comprising a handle secured to said housing for rotating said housing.

6. The endoscope as recited in claim 1, wherein said guidance sleeve has a first longitudinal slot in its outer surface which extends from close to or at the proximal end of said guidance sleeve to close to or at the distal end of said guidance sleeve and said housing has a bore extending radially outward from said guidance sleeve, said endoscope further comprising a locking mechanism disposed in said housing for locking said cylindrical guidance part and said guidance sleeve to one another for concomitant rotation, said locking mechanism including a locking pin slidably disposed in said bore adjacent said guidance sleeve with one end disposable in said longitudinal slot for locking said guidance sleeve and said cylindrical guidance part to one another, a compression spring in said bore in operative engagement with the end of said locking pin remote from said guidance sleeve for urging said locking pin into said longitudinal slot, a closure for holding said compression spring in said bore, and an operating element connected to said locking pin for retracting said locking pin from said longitudinal slot for permitting relative rotary movement between said guidance part and said guidance sleeve.

7. The endoscope as recited in claim 6, further comprising means for releasably holding said operating element for preventing retraction of said locking pin from said longitudinal slot.

8. The endoscope as recited in claim 6, wherein said guidance sleeve has a second longitudinal slot into which said locking pin can fit, said second longitudinal slot being spaced from said first longitudinal slot about the periphery of said guidance sleeve.

9. The endoscope as recited in claim 8, wherein said first longitudinal slot and said second longitudinal slot are spaced from one another by 180° degrees.

10. The endoscope as recited in claim 6, wherein said first longitudinal slot comprises a plurality of longitudinal slots into which said locking pin can fit, each longitudinal slot of said plurality of longitudinal slots being equally spaced from one another along the circumference of said guidance sleeve.

11. The endoscope of claim 1, further comprising a locking mechanism for locking said cylindrical guidance part to said guidance sleeve for concomitant rotation and for unlocking said guidance part from said guidance sleeve for independent rotation.

12. The endoscope as recited in claim 1, wherein the distal end of said probe has an opening therethrough for permitting viewing by an optical system.

13. The endoscope as recited in claim 1, further comprising an optical system, said optical system being axially disposed within said proximal end of said probe.

* * * * *